United States Patent [19]

D'Ovidio et al.

[11] Patent Number: 5,973,225
[45] Date of Patent: Oct. 26, 1999

[54] ISOLATION AND CHARACTERIZATION OF A GENE ENCODING A LOW MOLECULAR WEIGHT GLUTENIN

[75] Inventors: Renato D'Ovidio; Enrico Porceddu, both of Viterbo; Cinzia Marchitelli, Rome; Luisa Ercoli Cardelli, Viterbo, all of Italy

[73] Assignee: Ministero dell'università e della Ricerca Scientifica, Rome, Italy

[21] Appl. No.: 08/991,300

[22] Filed: Dec. 16, 1997

[30] Foreign Application Priority Data

Dec. 17, 1996 [IT] Italy ............................. MI96A2663

[51] Int. Cl.$^6$ ........................... A01H 5/00; C12N 15/29; C12N 15/70; C12N 15/82
[52] U.S. Cl. ................... 800/278; 435/468; 435/252.33; 435/320.1; 435/252.3; 536/23.6; 800/298; 800/320.3
[58] Field of Search ................. 536/23.6; 435/252.3, 435/252.33, 320.1, 419, 468, 471, 476, 488; 800/298, 320.3, 278, 295

[56] References Cited

PUBLICATIONS

Becker et al, Plant J., vol. 5, pp. 299–307, 1994.
Blechl et al, Nature Biotech., vol. 14, pp. 875–879, 1996.
Potrykus, I., Ann. Rev. Plant Physiol. Plant Mol. Biol., vol. 42, pp. 205–225, 1991.
D'Ovidio, R., Plant Mol. Biol., vol. 22, pp. 1173–1176, 1993.
Miller H., Meth. of Enzymol., vol. 152, pp. 145–170, 1987.
Greene et al, Meth. of Enzymol., vol. 152, pp. 512–522, 1987.
Barnes, W.M., Meth. of Enzymol., vol. 152, pp. 538–556, 1987.
Shatzman et al, Meth. of Enzymol., vol. 152, pp. 661–673, 1987.
Christou, P., Meth. Cell Biol., vol. 50, pp. 375–382, 1995.
Aryan et al, Mol. Gen. Genet., vol. 225, pp. 65–71, 1991.

*Primary Examiner*—David T. Fox
*Assistant Examiner*—Ashwin D. Mehta
*Attorney, Agent, or Firm*—Oblon, Spivak, McClelland, Maier & Neustadt, P.C.

[57] ABSTRACT

A description follows of the isolation and characterization of a gene which encodes a low molecular weight glutenin strictly correlated with the good qualitative characteristics of durum wheat meal and bran, a recombinant vector comprising said gene, a microorganism transformed with this vector and transgenic plants comprising said gene.

6 Claims, No Drawings

ISOLATION AND CHARACTERIZATION OF A GENE ENCODING A LOW MOLECULAR WEIGHT GLUTENIN

The present invention relates to a cloned and sequenced gene which encodes a low molecular weight glutenin correlated with the good qualitative characteristics of durum wheat meal and bran, a recombinant vector comprising said gene, a microorganism transformed with this vector and transgenic plants comprising said gene.

BACKGROUND OF THE INVENTION

It is known that the storage proteins of wheat have a fundamental role in determining the nutritive, bread-making and dough-making properties of meal. The main storage proteins are classified as gliadins and glutenins on the basis of their solubility in aqueous solvents, molecular weight and amino acid composition.

Gliadins are monomeric molecules with a low molecular weight (30–70 Kilodaltons) which can be separated by electrophoresis on polyacrylamide gel in an acid buffer and are categorized into four groups ($\alpha$, $\beta$, $\gamma$ and $\omega$) in decreasing order of mobility. On the basis of their N-terminal amino acid sequence, they are divided into three types $\alpha$, $\gamma$ and $\omega$; the first two groups contain residues of cysteine which form intermolecular disulfide bonds, whereas $\omega$-gliadins do not contain sulfurated amino acids.

Glutenins, on the other hand, are protein aggregates with a high molecular weight consisting of various polypeptide chains held together by intermolecular disulfide bonds. After reduction and separation by electrophoresis, they consist of subunits with a high (80–120 Kd) (HMW) and low (40–55 Kd) (LMW) molecular weight.

The high molecular weight subunits differ from gliadins not only in this characteristic but also in a greater content of glycine and a lower content of proline. The low molecular weight subunits resemble gliadins in their amino acid composition and molecular weight but are capable of forming intermolecular disulfide bridges and of binding themselves to the high molecular weight glutenin subunits, forming aggregates which are insoluble in alcohol solutions.

Although almost all the storage proteins of wheat participate in the formation of gluten, biochemical and genetic evidence shows that glutenin subunits with a low and high molecular weight play a fundamental role in determining the viscoelastic properties of gluten.

In particular, it has been shown that the presence of specific low molecular weight glutenins, called LMW-2, are responsible for the good qualitative characteristics of durum wheat (Pogna et al., (1990), J. Cereal Sci. 11, 15–34), whereas in soft wheat the qualitative characteristics are linked to the presence of the allelic pair of high molecular weight glutenins called Dx5-Dy10 (Payne et al. (1987)).

Analysis of the proteins of caryopses of wheat progeny deriving from intervarietal breeding and aneuploid lines has made it possible to localize the genes encoding the storage proteins on chromosomes and determine their heredity. In particular, the genes which encode glutenin subunits with a high molecular weight are localized on the long arms of chromosomes 1A and 1B, in complex loci indicated as Glu-1A and Glu-1B.

The low molecular weight glutenins are controlled by numerous genes situated on the Glu-3 loci of the short arm of chromosomes of group 1 of both genomes A and B and are strictly associated with the $\gamma$-gliadin genes (Gli-1).

The genes which encode some high molecular weight proteins and $\alpha$, $\beta$ and $\gamma$ gliadins have recently been sequenced.

With respect to the genes which encode the low molecular weight glutenin subunits, analysis is limited to a few members of the family and in particular those which encode LMW-2 have not yet been isolated.

SUMMARY OF THE INVENTION

A gene correlated with the glutenin subunits called LMW-2 has now been isolated, which encodes a low molecular weight protein strictly correlated with the technological characteristics of durum wheat meal and bran. The gene of the present invention can be used in genetic transformation programs of wheat suitable for obtaining wheat lines with improved qualitative characteristics.

DETAILED DESCRIPTION OF THE INVENTION

In accordance with this, one object of the present invention relates to a cloned and sequenced gene which encodes a low molecular weight protein strictly correlated with the technological characteristics of durum wheat bran and meal.

Another object of the present invention relates to a recombinant expression vector in host cells comprising this gene.

A further object of the present invention relates to a host microorganism transformed with this vector.

Another object of the present invention relates to transgenic plants transformed with said vector.

Further objects of the present invention will appear evident from reading the description and examples.

In particular, the gene of the present invention was isolated from the genomic DNA of a durum wheat line (*Triticum durum* L.) with excellent qualitative characteristics. For this purpose the known methods can be used, such as analysis of genomic library and polymerase chain amplification reactions (PCR).

The gene was preferably isolated by amplification of the genomic DNA obtained from *Triticum durum* L. by PCR, using suitable oligonucleotides as primers.

Operating as described above, a DNA fragment of 1107 bp was isolated, which corresponds to the whole region encoding the mature protein of 369 amino acids, with a molecular weight of 42242 daltons.

The nucleotide and amino acid sequences of the gene were compared with the sequences of other LMW genes at present available, and in particular the comparison was carried out with the two sequences available from durum wheat (Cassidy and Dovarak, 1991, Theor.Appl.Genet., 81:653–660; D'Ovidio et al., 1992, Plant Mol.Biol. 18:781–784). The result of the comparison showed a high degree of homology at both a nucleotide and amino acid level. In particular 71% and 73% respectively of identity with the clone pLMW21 (D'Ovidio et al. 1992) and the clone pTdUCD1 (Cassidy and Dovarak, 1991) was observed from the comparison of the amino acid sequences. The isoelectric point (pI=8.32) is slightly higher than that of the other two proteins encoded by the genes LMW21 (pI=7.86) and TdUCD1 (pI=7.54).

It is interesting to note that the protein encoded by the gene of the present invention has higher molecular dimensions than those of the other low molecular weight glutenins described so far in literature; these greater dimensions can be mainly attributed to the presence of an extensive repeated region between positions 56 and 169. In addition, the protein encoded by this gene has a cysteine residue in the repeated region and not in the initial part of the N-terminal region as observed in the other known LMW subunits.

The gene of the present invention can be cloned in a plant expression vector by positioning it under the control of specific regulation sequences (promoter and terminator) of the genes encoding the storage protein.

In fact vectors are available which contain specific endosperm promoter regions which have been successfully used in the transformation of wheat with genes encoding high molecular weight glutenin subunits (Blechl E. A. and Anderson O. D., 1996, Nature Biotech., 14:825–829).

The gene of the present invention can also be used as a probe for studying the variability in genetic materials and for identifying new allelic forms.

The plasmid pLMW-1CL containing the gene of the present invention was deposited as *E.coli* LMW-1CL at the Centraalbureau voor Schimmelcultures where it received the deposit number CBS 999.96.

Some illustrative but non-limiting examples are provided for a better understanding of the present invention.

EXAMPLE 1

Isolation of the gene (A) Extraction of the genomic DNA 5 g of leaves from a durum wheat line (*Triticum durum* L.) were introduced in a 50 ml Corning tube containing 45 ml of solution A having the following composition:

| | |
|---|---|
| sucrose | 0.5M |
| Tris-HCl | 10 mM, pH 8.0 |
| KCl | 80 mM |
| spermidine | 1 mM |
| spermine | 4 mM |
| EDTA | 10 mM. |

The plant material was homogenized at room temperature, repeating the operation 4 times for 5 seconds at medium velocity. The homogenized product was filtered on gauze and Miracloth$^R$ paper (Calbiochem) and then centrifuged at 1000×g for 20 minutes in an S34 rotor model Sorvall RC-5B, at 4C.

The pellet thus obtained was washed with 30 ml of solution B (solution A+0.5% Triton$^R$ x-100) and, after centrifugation at 1000×g for 20 minutes, it was resuspended in 20 ml of solution B.

After centrifugation at 1000×g for 15 minutes, the pellet was recovered and resuspended in 1 ml of buffer solution C (Tris-HCl 50 mM pH 8, 10 mM EDTA, 10 mM NaCl) containing 300 μl of Proteinase K (2 mg/ml). The suspension was maintained under bland stirring at 37° C. for 30 minutes, Sodiumdodecylsulfate (SDS) was added at a final concentration of 1% and maintained at 60° C. for 30 minutes.

After lysing the nuclei by adding 4 ml of solution D (solution C+0.5% SDS), the product was delicately mixed and incubated at 60° C. for 30 minutes. The solution was then extracted with phenol-chloroform and the genomic DNA was precipitated with cold absolute ethanol (−20° C.), collected with a glass rod and resuspended in 1 ml of TE buffer (10 mM Tris-HCl, pH 8.0 and 0.1 mM EDTA). The quantity of genomic DNA, evaluated by spectrophotometric reading using a Perkin-Elmer spectrophotometer mod 480 was 1 mg/ml.

(B) Amplification

With the aim of isolating the genes correlated with the LMW called LMW-2, the genomic DNA obtained as in step (a) was amplified by the Polymerase Chain Reaction (PCR) technique, according to the indications provided by Saiki et al., 1988, Science, 239:487–491, using the following pair of oligonucleotides as primers:

(1) 5' CGT TGC GGC GAC AAG TGC AA 3' (SEQ ID no:3)
(2) 5' GTA GGC ACC AAC TCC GGT GC 3' (SEQ ID no:4)

The amplification was carried out in a DNA Thermal Cycler$^R$ 480 apparatus (Perkin-Elmer Cetus) using a reaction mixture (100 l) containing:
150 ng of genomic DNA,
10 mM Tris HCl pH 8.3,
1.5 mM MgCl$_2$,
50 mM KCl,
0.01% (weight/volume) of gelatine,
250 ng of the two primers,
200 m of each deoxyribonucleotide (dNTP) and
2.5 Units of Taq DNA polymerase (Perkin Elmer).

After adding a drop of mineral oil, the cyclic program was started, which comprises:
1 minute at 94° C. (denaturing)
1 minute at 62° C. (annealing)
1 minute at 72° C. (extension)
for a total of 30 cycles, followed by 7 minutes at 72° C. (final extension).

The amplification product thus obtained was treated with phenol-chloroform (1:1), precipitated with sodium acetate 3 M (1/10 vol/vol) and EtOH (2 volumes) and resuspended in 20 l of H$_2$O. After purification on low-melting gel (SeaPlaque, FMC BioProducts) at 1.0% a DNA fragment of about 1200 bp was isolated.

The nucleotide sequence of the terminal regions of this fragment was then determined by direct sequencing of the amplified product. On the basis of the sequences obtained a pair of oligonucleotides were synthesized, having the following sequences:

g) 5' AGC CAT ATC CCT GGT TTG GAG 3' (SEQ ID no:5)
h) 5' CCG GAG TTG GTG CCT ACT TA 3' (SEQ ID no:6)

The fragment of 1200 bases was amplified with this pair, situated a few tens of bases downstream from the first pair. The amplification product (100 ng) was then cloned in the plasmid pGEM-T (PROMEGA) (50 ng) in 10 l of ligation mixture containing 1 unit of T4 DNA ligase. The reaction was carried out at 15° C. for 18 hours.

(C) Transformation of *E.coli*

5 l of the ligation mixture were used to transform 200 μl of cells of *E.coli* xL1-Blue-MRF' (Stratagene, Calif., U.S.A.) made competent with CaCl$_2$ (Dagert and Ehrlich, Gene, 6:23, 1979). The transformation reaction was carried out in ice for minutes, at 42° C. for 1.5 minutes and then again in ice for 10 minutes.

1 ml of LB medium (10 g/l Bacto tryptone$^R$ (DIFCO), 10 g/l NaCl and 5 g/l of yeast extract) was added to the reaction mixture which was incubated at 37° C. for 1 hour.

After centrifugation at 14,000 rpm for 30 minutes, the cells were recovered and resuspended in 200 μl of LB medium with which a plate of LB agar containing 40 μg/ml of X-Gal (5-bromo-4-chloro-3-indolyl-D-thiogalactopyranoside), 125 μg/ml of IPTG (isopropyl-beta-D-thiogalactcopyranoside) and 100 μg/ml of ampicilline, was inoculated. The plate was incubated at 37° C. for 16 hours.

(D) Extraction of the plasmid DNA

The white ampicilline-resistant colonies were removed and used to inoculate Eppendorf tubes containing 1.5 ml of LB to which 100 μg/ml of ampicilline had been added. The tubes were incubated under bland stirring (200 rpm) at 37° C. for 18 hours.

The bacterial culture was centrifuged at 14,000 rpm for 1 minute. After removing of the supernatant, the pellet was suspended in 150 μl of SET buffer (50 mM Tris HCl pH 8.0, 50 mM EDTA and 20% of sucrose). After adding 350 μl of lithic solution (0.2 M NaOH and 1% SDS), the samples were maintained in ice for 10 minutes.

250 μl of potassium acetate 3 M pH 4.8 were then added to each sample which was incubated in ice for 20 minutes and centrifuged for 10 minutes at 14,000 rpm. Absolute ethanol was added to the supernatant which was centrifuged for 10 minutes at 14,000 rpm. The pellet, recovered after decanting the supernatant, was dried in a vacuum pump for 10 minutes and resuspended in 20 ml of TE pH 8. One of the positive clones was called LMW-1CL.

EXAMPLE 2

To verify the nature of the amplification products and recombinant plasmids Southern blot experiments were carried out using as probe the clone pLMW21 comprising a gene (856 bp) which encodes a LMW-GS subunit (R. D'Ovidio et al. (1992), Plant Mol. Biol. 18:781–784).

A) Preparation of the probe

The fragment corresponding to the above gene was amplified by PCR, operating as described in example 1, and purified with the Quiaquick-spin$^R$ system (Quiagen) by adding 0.5 volumes of PB (Binding buffer) and applying the solution to a Quiaquick spin column. The column was centrifugated for 60 seconds and then washed with PE (washing solution, Quiagen). This solution was removed by centrifugation for 60 seconds and the DNA was eluted with 50 μl of 10 mM Tris-HCl pH 8.5.

700 ng of the DNA thus purified were labelled by Nick Translation operating according to the standard technique (Sambrook et al., 1989, Molecular Cloning: A laboratory Manual, Cold Spring Harbor laboratory Press). The labelled DNA was recovered by centrifugation, resuspended in μl 50 of TE buffer (10 mM Tris-HCl pH 8.1, 1 mM EDTA pH 8) and used in the hybridization experiments.

B) Molecular hybridizations

The insert contained in the recombinant clones was amplified by PCR following the conditions described above.

The reaction mixtures were charged onto agarose gel at 1.2% in a TBE 1x buffer (0.089 M Tris-HCl, 0.089 M boric acid, 0.02 M EDTA) and run at 100 volts for 2 hours. The DNA bands, visualized by colouring with ethidium bromide (0.5 g/ml), were then transferred onto a nylon filter (Amersham) according to the Southern blot technique (Maniatis et al., "Molecular Cloning: a practical laboratory manual", Cold Spring Harbor, N.Y., 1982).

The hybridization reaction was carried out in plastic boxes at 67° C. in a solution containing 0.02% (w/v) of SDS, 0.1% (w/v) of N-lauroylsarcosine, 5xSSC and 0.5% (w/v) of blocking reagent (Boehringer).

The filters were hybridized with the labelled probe in the presence of digoxygenine. After hybridization, the filters were washed twice with 2xSSC (0.3 M NaCl and 0.3 M Na-citrate pH 7) and 0.1% (w/v) of SDS for 5 minutes at room temperature and twice with 1xSSC and 0.1% (w/v) of SDS for 15 minutes at 67° C.

The survey of complete hybridization between homologous sequences was carried out using the following solutions:
solution 1: 100 mM Tris-HCl pH 7.5 and 150 mM NaCl
solution 2: solution 1+1% blocking reagent (Boehringer)
solution 3: 100 mM Tris-HCl pH 9.5, 100 mM HCl and 50 mM MgCl
solution 4: 10 mM Tris-HCl pH 8 and 1 mM EDTA.

The filter was washed with solution 1, then incubated for 30 minutes in solution 2 in the presence of the antibody antidigoxygenine-AP (Boehringer) in a ratio of 1 μl for each 10 ml of solution 2. The excess antibody was removed with two 15 minute washings in solution 1 and the filter was then equilibrated for 3 minutes in solution 3. All the phases described above were carried out under stirring and at room temperature. Finally the filter was covered with the colouring solution (45 μl of NBT-solution and 35 μl of x-phosphate solution in 10 ml of solution 3) and placed in the dark to allow the reaction to take place. At the end, the excess colouring solution was removed and the filter washed with solution 4. The hybridization reaction with the probe gave positive results.

EXAMPLE 3

Characterization of the gene

The nucleotide sequence was determined using as a model both the amplification product of the 1200 bp fragment and the plasmid clone pLMW-1CL with the Taq DNA polymerase according to the instructions of the manufacturer (Perkin Elmer).

The nucleotide sequence of this gene consists of 1107 bp (SEQ ID no:1) and corresponds to the whole region encoding the mature protein (SEQ ID no:2). The deduced amino acid sequence consists of 369 amino acids with a molecular weight of 42242 daltons and an isoelectric point (PI) of 8.32.

In compliance with what has been observed for this group of reserve proteins, analysis of the amino acid composition (table 1) showed the presence of a high content of glutamine (36%) and proline (17%).

TABLE 1

| Aminoacid | Nb | % |
|---|---|---|
| Ala | 8 | 1.9 |
| Arg | 7 | 1.6 |
| Asn | 3 | 0.7 |
| Asp | 0 | 0 |
| Cys | 8 | 1.9 |
| Gln | 146 | 35.2 |
| Glu | 4 | 0.9 |
| Gly | 9 | 2.1 |
| His | 9 | 2.1 |
| Ile | 13 | 3.1 |
| Leu | 35 | 8.4 |
| Lys | 1 | 0.2 |
| Met | 5 | 1.2 |
| Phe | 23 | 5.5 |
| Pro | 71 | 17.1 |
| Ser | 39 | 9.4 |
| Thr | 10 | 2.4 |
| Trp | 2 | 0.4 |
| Tyr | 4 | 0.9 |
| Val | 17 | 4.1 |

The nucleotide and amino acid sequences of the LMW-1CL gene were compared with the sequences of the other LMW-GS genes at present available, and in particular the comparison was carried out with the two available sequences of durum wheat (Cassidy and Dovarak, 1991; D'Ovidio et al., 1992). The result of the comparative analysis showed a high degree of homology both at a nucleotide and amino acid level. In particular from a comparison of the amino acid sequences, 71% and 73% respectively of identity with the clone pLMW21 (D'Ovidio et al. 1992) and the clone pTdUCD1 (Cassidy and Dovarak, 1991) was observed.

The isoelectric point of the protein of the present invention is slightly higher than that of the other two proteins encoded by the genes LMW21 (pI=7.86) and TdUCD1 (pI=7.54).

It is interesting to note that the protein has higher molecular dimensions with respect to those of the other low molecular weight glutenins cited so far in literature; these greater dimensions can be mainly attributed to the presence of an extensive repeated region between positions 56 and 194. In addition, the protein encoded by this gene has a cysteine residue in the repeated region and not in the initial part of the N-terminal region as observed in the other known LMW subunits.

Evidence of the correlation existing between the gene of the present invention and the LMW-2 glutenin subunits derives from the following observations:

the amplification product contained in the clone PLMW-1CL is only present in the cultivar which have LMW-2 glutenin subunits the molecular weight of the protein encoded by the gene (42242) corresponds to that estimated on the polyacrylamide gel containing SDS (SDS-PAGE) for the LMW2 glutenin subunits (45,000).

We claim:

1. An isolated gene from the genomic DNA of *Triticum durum* L. consisting of the nucleotide sequence SEQ ID NO: 1.

2. A recombinant expression vector comprising the gene of claim 1.

3. The vector according to claim 2, deposited as *E.coli* LMW-1C1 with deposit number CBS 999.96.

4. A microorganism transformed with the recombinant expression vector of claim 2.

5. A plant transformed with the isolated gene of claim 1.

6. Seeds obtained from the plant of claim 5.

* * * * *

UNITED STATES PATENT AND TRADEMARK OFFICE
CERTIFICATE OF CORRECTION

PATENT NO. : 5,973,225
DATED : October 26, 1999
INVENTOR(S) : Renato D'OVIDIO et al.

It is certified that error appears in the above-identified patent and that said Letters Patent is hereby corrected as shown below:

On the title page, item [30] should be:

--[30] Foreign Application Priority Data

Dec. 19, 1996 [IT] Italy.................MI96A2663--

Signed and Sealed this

Twelfth Day of December, 2000

Attest:

Q. TODD DICKINSON

*Attesting Officer*  *Director of Patents and Trademarks*

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1107 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
AGCCATATCC CTGGTTTGGA GAGACCATCG CAGCAACAAC CATTACCACC ACAACAAACA      60

TTATCGCACC ACCACCAACA ACAACCCATC CAACAACAAC CACACCAATT TCCACAACAG     120

CAACCATGTT CACAGCAACA ACAACAACCA CCATTATCGC AACAACAACA ACCACCATTT     180

TCGCAGCAAC AACAACCACC ATTTTCACAG CAACAACAAC CAGTTCTACC GCAACAACCA     240

TCATTTTCGC AGCAACAACT ACCACCATTT TCGCAGCAAC AACAACCACC ATTTTCACAG     300

CAACAACAAC CAGTTCTACC GCAACAACCA TCATTTTCGC AGCAACAACT ACCACCATTT     360

TCACAGCAAC TACCACCATT TTCGCAGCAA CAACCAGTAC TACCGCAACA ACCACCATTT     420

TCGCAGCAAC AACCACCACC ATTTTCACAG CAACTACCAC CATTTTCGCA GCAACAACAA     480

CCAGTACTAC CGCAACAACC ACCATTTTCG CAACAACAAC AACAACCAAT TCCACCGCAA     540

CAACCACCAT TTTCGCAACA ACAACAGCCA GTTCTACTGC AACAACAAAT ACCATTTGTT     600

CATCCATCTA TCTTGCAGCA ACTAAACCCA TGCAAGGTAT TCCTCCAGCA GCAATGCAGC     660

CCTTGGGCTA TGCCACAAAG TCTTGCTAGG TCGCAAATGT TGCAGCAGAG CAGTTGCCAT     720

GTGATGCAAC AACAATGTTG CCAGCAGTTG CCGCAAATAC CCCAGCAATC CCGCTATGAG     780

GCAATCCGTG CTATCGTCTA CTCCATCATC CTGCAAGAAC AACAACAGGT TCAGGGTTCC     840

ATCCAAACTC AGCAGCAGCA ACCCCAACAG TTGGGCCAAT GCGTTTCCCA ACCCCAACAA     900

CAGTCGCAAC AGCAACTCGG GCAACAACCT CAACAACAAC AATTGGCACA TGGTACCTTT     960

TTGCAGCCAC ACCAAATAGC TCAGCTTGAG GTGATGACTT CCATTGCGCT CCGTACCCTG    1020

CCAACAATGT GCAATTGGAA TGTGCCGTTG TATAGAACCA CCACTAGGGT GCCATTCGGC    1080

GTTGGCACCG GAGTTGGTGC CTACTTA                                       1107
```

(2) INFORMATION FOR SEQ ID NO:2:

(i) SEQUENCE CHARACTERISTICS:
      (A) LENGTH: 369 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:2:

```
Ser His Ile Pro Gly Leu Glu Arg Pro Ser Gln Gln Gln Pro Leu Pro
 1               5                  10                  15
Pro Gln Gln Thr Leu Ser His His Gln Gln Gln Pro Ile Gln Gln
             20                  25                  30
Gln Pro His Gln Phe Pro Gln Gln Pro Cys Ser Gln Gln Gln Gln
         35                  40                  45
Gln Pro Pro Leu Ser Gln Gln Gln Pro Pro Phe Ser Gln Gln Gln
 50                  55                  60
Gln Pro Pro Phe Ser Gln Gln Gln Pro Val Leu Pro Gln Pro
 65                  70                  75                  80
Ser Phe Ser Gln Gln Gln Leu Pro Pro Phe Ser Gln Gln Gln Pro
             85                  90                  95
Pro Phe Ser Gln Gln Gln Pro Val Leu Pro Gln Gln Pro Ser Phe
         100                 105                 110
Ser Gln Gln Gln Leu Pro Pro Phe Ser Gln Gln Leu Pro Pro Phe Ser
             115                 120                 125
Gln Gln Gln Pro Val Leu Pro Gln Gln Pro Phe Ser Gln Gln Gln
 130                 135                 140
Pro Pro Pro Phe Ser Gln Gln Leu Pro Pro Phe Ser Gln Gln Gln Gln
 145                 150                 155                 160
Pro Val Leu Pro Gln Gln Pro Phe Ser Gln Gln Gln Gln Pro
             165                 170                 175
Ile Pro Pro Gln Gln Pro Pro Phe Ser Gln Gln Gln Pro Val Leu
             180                 185                 190
Leu Gln Gln Gln Ile Pro Phe Val His Pro Ser Ile Leu Gln Gln Leu
         195                 200                 205
Asn Pro Cys Lys Val Phe Leu Gln Gln Gln Cys Ser Pro Trp Ala Met
         210                 215                 220
Pro Gln Ser Leu Ala Arg Ser Gln Met Leu Gln Gln Ser Ser Cys His
225                 230                 235                 240
Val Met Gln Gln Gln Cys Cys Gln Gln Leu Pro Gln Ile Pro Gln Gln
             245                 250                 255
Ser Arg Tyr Glu Ala Ile Arg Ala Ile Val Tyr Ser Ile Ile Leu Gln
             260                 265                 270
Glu Gln Gln Gln Val Gln Gly Ser Ile Gln Thr Gln Gln Gln Pro
         275                 280                 285
Gln Gln Leu Gly Gln Cys Val Ser Gln Pro Gln Gln Ser Gln Gln
         290                 295                 300
Gln Leu Gly Gln Gln Pro Gln Gln Gln Leu Ala His Gly Thr Phe
305                 310                 315                 320
Leu Gln Pro His Gln Ile Ala Gln Leu Glu Val Met Thr Ser Ile Ala
             325                 330                 335
Leu Arg Thr Leu Pro Thr Met Cys Asn Trp Asn Val Pro Leu Tyr Arg
             340                 345                 350
Thr Thr Thr Arg Val Pro Phe Gly Val Gly Thr Gly Val Gly Ala Tyr
             355                 360                 365
Leu
```

(2) INFORMATION FOR SEQ ID NO:3:

(i) SEQUENCE CHARACTERISTICS:
(A) LENGTH: 20 base pairs (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(xi) SEQUENCE DESCRIPTION: SEQ ID NO:3:

CGTTGCGGCG ACAAGTGCAA                                                    20

(2) INFORMATION FOR SEQ ID NO:4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(xi) SEQUENCE DESCRIPTION: SEQ ID NO:4:

GTAGGCACCA ACTCCGGTGC                                                    20

(2) INFORMATION FOR SEQ ID NO:5:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(xi) SEQUENCE DESCRIPTION: SEQ ID NO:5:

AGCCATATCC CTGGTTTGGA G                                                  21

(2) INFORMATION FOR SEQ ID NO:6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(xi) SEQUENCE DESCRIPTION: SEQ ID NO:6:

CCGGAGTTGG TGCCTACTTA                                                    20